(12) United States Patent
Honaryar et al.

(10) Patent No.: US 8,715,158 B2
(45) Date of Patent: May 6, 2014

(54) IMPLANTABLE BOTTOM EXIT PORT

(75) Inventors: Babak Honaryar, Orinda, CA (US);
Marcos Borrell, Goleta, CA (US);
Christopher S. Mudd, Goleta, CA (US);
Joseph S. Raven, Goleta, CA (US); Jeff Allen, Crestwood, KY (US); Sean Snow, Goleta, CA (US); Vernon L. Vincent, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 435 days.

(21) Appl. No.: 13/021,099

(22) Filed: Feb. 4, 2011

(65) Prior Publication Data
US 2011/0218392 A1   Sep. 8, 2011

Related U.S. Application Data

(63) Continuation-in-part of application No. 12/904,422, filed on Oct. 14, 2010, which is a continuation-in-part of application No. 12/772,039, filed on Apr. 30, 2010.

(60) Provisional application No. 61/237,641, filed on Aug. 27, 2009, provisional application No. 61/236,869, filed on Aug. 26, 2009.

(51) Int. Cl.
*A61F 2/04* (2013.01)

(52) U.S. Cl.
USPC ............................................. 600/37; 604/174

(58) Field of Classification Search
USPC ................. 604/174; 600/29, 30, 31, 32, 37
See application file for complete search history.

(56) References Cited

U.S. PATENT DOCUMENTS

| | | |
|---|---|---|
| 586,113 A | 7/1897 | Bott |
| 2,163,048 A | 6/1939 | McKee |
| 2,737,954 A | 3/1956 | Knapp |
| 3,371,352 A | 3/1968 | Siposs et al. |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,840,018 A | 10/1974 | Heifetz |
| 3,958,562 A | 5/1976 | Hakim et al. |
| 3,971,376 A | 7/1976 | Wichterle |
| 4,019,499 A | 4/1977 | Fitzgerald |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Helioscopie Product Insert for Heliogast, pp. 1-11 (undated).

(Continued)

*Primary Examiner* — Christine Matthews
*Assistant Examiner* — Joshua D Lannu
(74) *Attorney, Agent, or Firm* — Gordon & Jacobson, PC

(57) ABSTRACT

The present invention provides a system for attaching a fluid access port to a patient. The system generally comprises an implantable access port with a bottom exit port and method for attaching an access port to a patient. In addition, a tube guard, flexible tube exit port, tissue guard, and porous coupling member are disclosed.

23 Claims, 7 Drawing Sheets

(56) References Cited

U.S. PATENT DOCUMENTS

| | | |
|---|---|---|
| 4,118,805 A | 10/1978 | Reimels |
| 4,151,835 A | 5/1979 | Showell et al. |
| 4,161,943 A | 7/1979 | Nogier |
| 4,164,943 A | 8/1979 | Hill et al. |
| 4,190,040 A | 2/1980 | Schulte |
| 4,233,992 A | 11/1980 | Bisping |
| 4,265,252 A | 5/1981 | Chubbuck et al. |
| 4,280,722 A | 7/1981 | Guptil et al. |
| 4,413,985 A | 11/1983 | Wellner |
| 4,474,572 A | 10/1984 | McNaughton et al. |
| 4,502,335 A | 3/1985 | Wamstad et al. |
| 4,543,088 A | 9/1985 | Bootman et al. |
| 4,557,722 A | 12/1985 | Harris |
| 4,569,675 A | 2/1986 | Prosl et al. |
| 4,588,394 A | 5/1986 | Schulte et al. |
| 4,592,339 A | 6/1986 | Kuzmak et al. |
| 4,592,355 A | 6/1986 | Antebi |
| 4,634,427 A | 1/1987 | Hannula et al. |
| 4,655,765 A | 4/1987 | Swift |
| 4,673,394 A | 6/1987 | Fenton, Jr. et al. |
| 4,692,146 A | 9/1987 | Hilger |
| 4,696,288 A | 9/1987 | Kuzmak et al. |
| 4,704,103 A | 11/1987 | Stober et al. |
| 4,710,174 A | 12/1987 | Moden et al. |
| 4,738,657 A | 4/1988 | Hancock et al. |
| 4,767,410 A | 8/1988 | Moden et al. |
| 4,772,270 A | 9/1988 | Wiita et al. |
| 4,778,452 A | 10/1988 | Moden et al. |
| 4,781,680 A | 11/1988 | Redmond et al. |
| 4,796,641 A | 1/1989 | Mills et al. |
| 4,802,885 A | 2/1989 | Weeks et al. |
| 4,832,054 A | 5/1989 | Bark |
| 4,840,615 A | 6/1989 | Hancock et al. |
| 4,850,227 A | 7/1989 | Luettgen et al. |
| 4,858,623 A | 8/1989 | Bradshaw et al. |
| 4,861,341 A | 8/1989 | Woodburn |
| 4,881,939 A | 11/1989 | Newman |
| 4,886,501 A | 12/1989 | Johnston et al. |
| 4,902,278 A | 2/1990 | Maget et al. |
| 4,904,241 A | 2/1990 | Bark |
| 4,913,702 A | 4/1990 | Yum et al. |
| 4,915,690 A | 4/1990 | Cone et al. |
| 4,929,230 A | 5/1990 | Pfleger |
| 4,929,236 A | 5/1990 | Sampson |
| 4,966,588 A | 10/1990 | Rayman et al. |
| 4,967,755 A | 11/1990 | Pohndorf |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melsky et al. |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan et al. |
| 5,098,397 A | 3/1992 | Svensson |
| 5,108,377 A | 4/1992 | Cone et al. |
| 5,125,408 A | 6/1992 | Basser |
| 5,133,753 A | 7/1992 | Bark et al. |
| 5,137,529 A | 8/1992 | Watson et al. |
| 5,147,483 A | 9/1992 | Melsky et al. |
| 5,152,747 A | 10/1992 | Olivier |
| 5,167,638 A | 12/1992 | Felix et al. |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber et al. |
| 5,250,026 A | 10/1993 | Ehrlich et al. |
| 5,273,537 A | 12/1993 | Haskvitz et al. |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg et al. |
| 5,337,747 A | 8/1994 | Neftel |
| 5,360,407 A | 11/1994 | Leonard et al. |
| 5,368,040 A | 11/1994 | Carney |
| 5,387,192 A | 2/1995 | Glantz et al. |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil, Jr. et al. |
| 5,540,648 A | 7/1996 | Yoon |
| 5,556,388 A | 9/1996 | Johlin, Jr. |
| 5,558,641 A | 9/1996 | Glantz et al. |
| 5,562,617 A | 10/1996 | Finch, Jr. et al. |
| 5,571,104 A | 11/1996 | Li |
| 5,575,777 A | 11/1996 | Cover et al. |
| 5,601,604 A | 2/1997 | Vincent |
| 5,637,102 A | 6/1997 | Tolkoff et al. |
| 5,653,755 A | 8/1997 | Ledergerber |
| 5,658,298 A | 8/1997 | Vincent et al. |
| 5,674,397 A | 10/1997 | Pawlak et al. |
| 5,683,447 A | 11/1997 | Bush et al. |
| 5,688,237 A | 11/1997 | Rozga et al. |
| 5,695,490 A | 12/1997 | Flaherty et al. |
| 5,716,342 A | 2/1998 | Dumbraveanu et al. |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin et al. |
| 5,814,019 A | 9/1998 | Steinbach et al. |
| 5,833,654 A | 11/1998 | Powers et al. |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen et al. |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank et al. |
| 5,932,460 A | 8/1999 | Mills et al. |
| 5,935,083 A | 8/1999 | Williams |
| 5,938,669 A | 8/1999 | Klaiber et al. |
| 5,951,512 A | 9/1999 | Dalton |
| 6,024,704 A | 2/2000 | Meador et al. |
| 6,030,369 A | 2/2000 | Engelson et al. |
| 6,039,712 A | 3/2000 | Fogarty et al. |
| 6,074,341 A | 6/2000 | Anderson et al. |
| 6,090,066 A | 7/2000 | Schnell |
| 6,098,405 A | 8/2000 | Miyata et al. |
| 6,102,678 A | 8/2000 | Peclat |
| 6,102,922 A | 8/2000 | Jakobsson et al. |
| 6,123,700 A | 9/2000 | Mills et al. |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen et al. |
| 6,221,024 B1 | 4/2001 | Miesel |
| 6,234,973 B1 | 5/2001 | Meador et al. |
| 6,258,079 B1 | 7/2001 | Burbank et al. |
| 6,264,676 B1 | 7/2001 | Gellman et al. |
| 6,270,475 B1 | 8/2001 | Bestetti |
| 6,283,949 B1 | 9/2001 | Roorda |
| 6,321,124 B1 | 11/2001 | Cigaina |
| 6,349,740 B1 | 2/2002 | Cho et al. |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda et al. |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent et al. |
| 6,572,587 B2 | 6/2003 | Lerman et al. |
| 6,589,184 B2 | 7/2003 | Noren et al. |
| 6,648,849 B2 | 11/2003 | Tenhuisen et al. |
| 6,666,845 B2 | 12/2003 | Hooper et al. |
| 6,689,100 B2 | 2/2004 | Connelly et al. |

(56) References Cited

U.S. PATENT DOCUMENTS

| | | |
|---|---|---|
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |
| 6,939,299 B1 | 9/2005 | Petersen et al. |
| 6,953,444 B2 | 10/2005 | Rosenberg |
| 6,964,204 B2 | 11/2005 | Clark et al. |
| 6,966,875 B1 | 11/2005 | Longobardi |
| 6,997,914 B2 | 2/2006 | Smith et al. |
| 7,017,583 B2 | 3/2006 | Forsell |
| 7,020,531 B1 | 3/2006 | Colliou et al. |
| 7,056,286 B2 | 6/2006 | Ravenscroft et al. |
| 7,063,669 B2 | 6/2006 | Brawner et al. |
| 7,073,387 B2 | 7/2006 | Zdeblick et al. |
| 7,082,843 B2 | 8/2006 | Clark et al. |
| 7,131,945 B2 | 11/2006 | Fink et al. |
| 7,144,400 B2 | 12/2006 | Byrum et al. |
| 7,149,587 B2 | 12/2006 | Wardle et al. |
| 7,191,007 B2 | 3/2007 | Desai et al. |
| 7,195,774 B2 | 3/2007 | Carvalho et al. |
| 7,223,239 B2 | 5/2007 | Schulze |
| 7,226,419 B2 | 6/2007 | Lane et al. |
| 7,261,003 B2 | 8/2007 | McDonald et al. |
| 7,267,645 B2 | 9/2007 | Anderson et al. |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum et al. |
| 7,351,226 B1 | 4/2008 | Herskowitz |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,367,937 B2 | 5/2008 | Jambor et al. |
| 7,374,557 B2 | 5/2008 | Conlon |
| 7,374,565 B2 | 5/2008 | Hassler, Jr. et al. |
| 7,390,294 B2 | 6/2008 | Hassler, Jr. |
| 7,413,547 B1 | 8/2008 | Lichtscheidl et al. |
| 7,416,528 B2 | 8/2008 | Crawford et al. |
| 7,437,951 B2 | 10/2008 | McDonald et al. |
| 7,438,718 B2 | 10/2008 | Milliman et al. |
| 7,445,614 B2 | 11/2008 | Bunodiere et al. |
| 7,468,038 B2 | 12/2008 | Ye et al. |
| 7,500,944 B2 | 3/2009 | Byrum et al. |
| 7,510,530 B2 | 3/2009 | Hashimoto et al. |
| 7,530,943 B2 | 5/2009 | Lechner |
| 7,553,298 B2 | 6/2009 | Hunt |
| 7,561,916 B2 | 7/2009 | Hunt |
| 7,580,746 B2 | 8/2009 | Gilkerson et al. |
| 7,591,185 B1 | 9/2009 | Mothilal et al. |
| 7,593,777 B2 | 9/2009 | Gerber |
| 7,634,319 B2 | 12/2009 | Schneider et al. |
| 7,651,483 B2 | 1/2010 | Byrum |
| 7,658,196 B2 | 2/2010 | Ferreri et al. |
| 7,699,770 B2 | 4/2010 | Hassler, Jr. et al. |
| 7,708,722 B2 | 5/2010 | Glenn |
| 7,762,998 B2 | 7/2010 | Birk et al. |
| 7,762,999 B2 | 7/2010 | Byrum |
| 7,775,215 B2 | 8/2010 | Hassler, Jr. et al. |
| 7,775,966 B2 | 8/2010 | Dlugos et al. |
| 7,811,275 B2 | 10/2010 | Birk et al. |
| 7,850,660 B2 | 12/2010 | Uth et al. |
| 7,862,546 B2 | 1/2011 | Conlon et al. |
| 7,909,754 B2 | 3/2011 | Hassler, Jr. et al. |
| 7,909,804 B2 | 3/2011 | Stats |
| 8,007,474 B2 | 8/2011 | Uth et al. |
| 2001/0052141 A1 | 12/2001 | Andersen |
| 2002/0013545 A1 | 1/2002 | Soltanpour et al. |
| 2002/0058969 A1 | 5/2002 | Noren et al. |
| 2002/0087147 A1 | 7/2002 | Hooper et al. |
| 2002/0095181 A1 | 7/2002 | Beyer |
| 2002/0139208 A1 | 10/2002 | Yatskov |
| 2002/0198548 A1 | 12/2002 | Robert |
| 2003/0045800 A1 | 3/2003 | Noren et al. |
| 2003/0045910 A1 | 3/2003 | Sorensen et al. |
| 2003/0073880 A1 | 4/2003 | Polsky et al. |
| 2003/0078506 A1 | 4/2003 | Noren et al. |
| 2003/0139690 A1 | 7/2003 | Aebli et al. |
| 2004/0064110 A1 | 4/2004 | Forsell |
| 2004/0065615 A1 | 4/2004 | Hooper et al. |
| 2004/0068233 A1 | 4/2004 | DiMatteo |
| 2004/0082908 A1 | 4/2004 | Whitehurst et al. |
| 2004/0111050 A1 | 6/2004 | Smedley et al. |
| 2004/0204692 A1 | 10/2004 | Eliasen |
| 2004/0254536 A1 | 12/2004 | Conlon et al. |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0010177 A1 | 1/2005 | Tsai |
| 2005/0049578 A1 | 3/2005 | Tu et al. |
| 2005/0070875 A1 | 3/2005 | Kulessa |
| 2005/0070937 A1 | 3/2005 | Jambor et al. |
| 2005/0085778 A1 | 4/2005 | Parks |
| 2005/0092093 A1 | 5/2005 | Kang et al. |
| 2005/0131325 A1 | 6/2005 | Chen et al. |
| 2005/0131352 A1 | 6/2005 | Conlon |
| 2005/0131383 A1 | 6/2005 | Chen et al. |
| 2005/0148956 A1 | 7/2005 | Conlon |
| 2005/0149143 A1 | 7/2005 | Libbus et al. |
| 2005/0209573 A1 | 9/2005 | Brugger et al. |
| 2005/0240155 A1 | 10/2005 | Conlon |
| 2005/0240156 A1* | 10/2005 | Conlon .................... 604/174 |
| 2005/0267500 A1 | 12/2005 | Hassler, Jr. et al. |
| 2005/0277899 A1 | 12/2005 | Conlon |
| 2005/0283041 A1 | 12/2005 | Egle |
| 2005/0283118 A1* | 12/2005 | Uth et al. ................ 604/175 |
| 2005/0283119 A1 | 12/2005 | Uth |
| 2006/0074439 A1 | 4/2006 | Garner et al. |
| 2006/0122578 A1 | 6/2006 | Lord et al. |
| 2006/0161186 A1 | 7/2006 | Hassler, Jr. et al. |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0189887 A1 | 8/2006 | Hassler, Jr. et al. |
| 2006/0189888 A1 | 8/2006 | Hassler, Jr. et al. |
| 2006/0190039 A1 | 8/2006 | Birk |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0217668 A1 | 9/2006 | Schulze et al. |
| 2006/0217673 A1* | 9/2006 | Schulze et al. .......... 604/288.02 |
| 2006/0235445 A1 | 10/2006 | Birk |
| 2006/0235448 A1 | 10/2006 | Roslin et al. |
| 2006/0247539 A1 | 11/2006 | Schugt et al. |
| 2006/0266128 A1 | 11/2006 | Clark et al. |
| 2006/0293625 A1 | 12/2006 | Hunt et al. |
| 2006/0293626 A1 | 12/2006 | Byrum et al. |
| 2006/0293627 A1 | 12/2006 | Byrum |
| 2006/0293628 A1 | 12/2006 | Hunt et al. |
| 2007/0010790 A1 | 1/2007 | Byrum et al. |
| 2007/0015954 A1 | 1/2007 | Dlugos |
| 2007/0015955 A1 | 1/2007 | Tsonton |
| 2007/0016231 A1 | 1/2007 | Jambor et al. |
| 2007/0027356 A1 | 2/2007 | Ortiz |
| 2007/0038255 A1 | 2/2007 | Kieval et al. |
| 2007/0060959 A1 | 3/2007 | Salo et al. |
| 2007/0073250 A1 | 3/2007 | Schneiter |
| 2007/0078391 A1 | 4/2007 | Wortley |
| 2007/0088336 A1 | 4/2007 | Dalton |
| 2007/0088391 A1 | 4/2007 | McAlexander |

(56) References Cited

U.S. PATENT DOCUMENTS

| | | |
|---|---|---|
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185462 A1 | 8/2007 | Byrum |
| 2007/0191717 A1 | 8/2007 | Rosen et al. |
| 2007/0205384 A1 | 9/2007 | Kurosawa |
| 2007/0208313 A1 | 9/2007 | Conlon |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0054407 A1 | 3/2011 | Olroyd et al. |
| 2011/0082426 A1 | 4/2011 | Conlon et al. |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |
| WO | WO 97/01370 | 1/1997 |
| WO | WO 99/20338 | 4/1999 |
| WO | WO 99/26543 | 6/1999 |
| WO | WO 99/34859 | 7/1999 |
| WO | WO 00/15158 | 3/2000 |
| WO | WO 00/33901 | 6/2000 |

(56) References Cited

FOREIGN PATENT DOCUMENTS

| WO | WO 01/10359 | 2/2001 |
| WO | WO 01/49245 | 7/2001 |
| WO | WO 01/80926 | 11/2001 |
| WO | WO 01/95813 | 12/2001 |
| WO | WO 02/10667 | 2/2002 |
| WO | WO 02/074381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS

Autumn K. et al.; "Evidence of Van Der Waals Adhesion in Gecko Setae"; PNAS; vol. 99; No. 19; pp. 12252-12256; Sep. 17, 2012.

Geim AK. et al.; "Microfabricated Adhesive Mimicking Gecko Foot-Hair"; Nature Materials Abstract only; vol. 2; No. 7; 2003.

Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.

Yurdumakan B., et al.; "Synthetic Gecko Foot-Hairs from Multiwalled Carbon Nanotubes"; The Royal Society of Chemistry; p. 3799-3801; 2005.

http://en/wikipedia.org/Injection_Molding, Accessed Sep. 6, 2012.

* cited by examiner

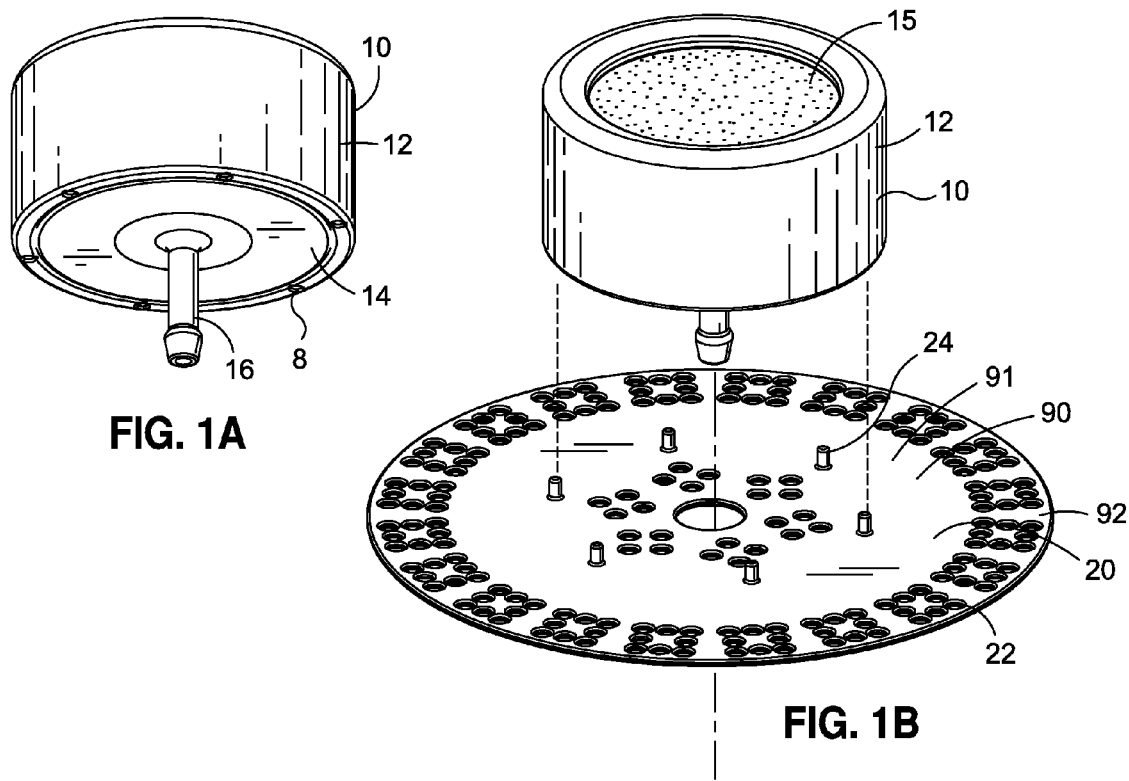
FIG. 1A
FIG. 1B
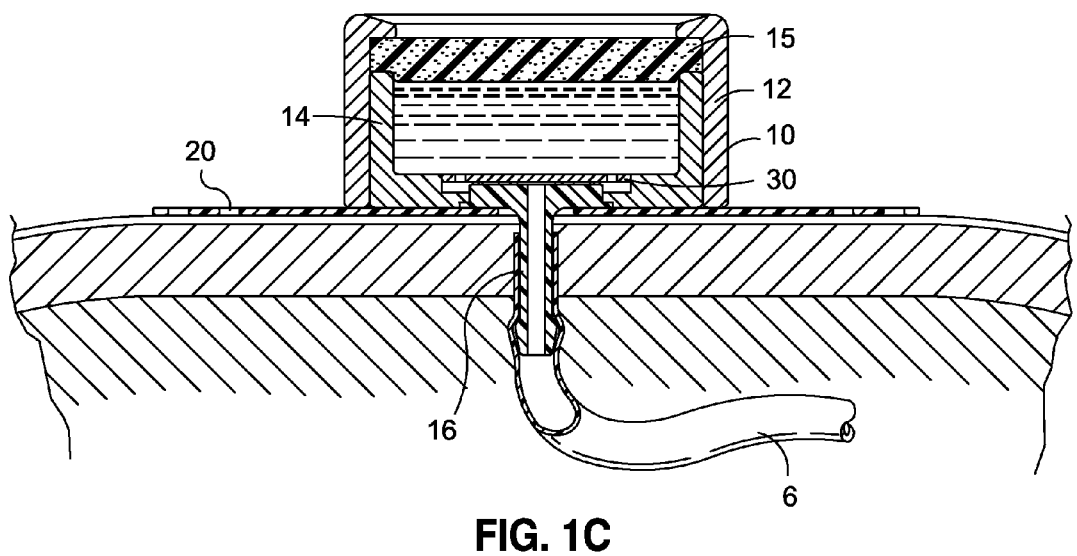
FIG. 1C

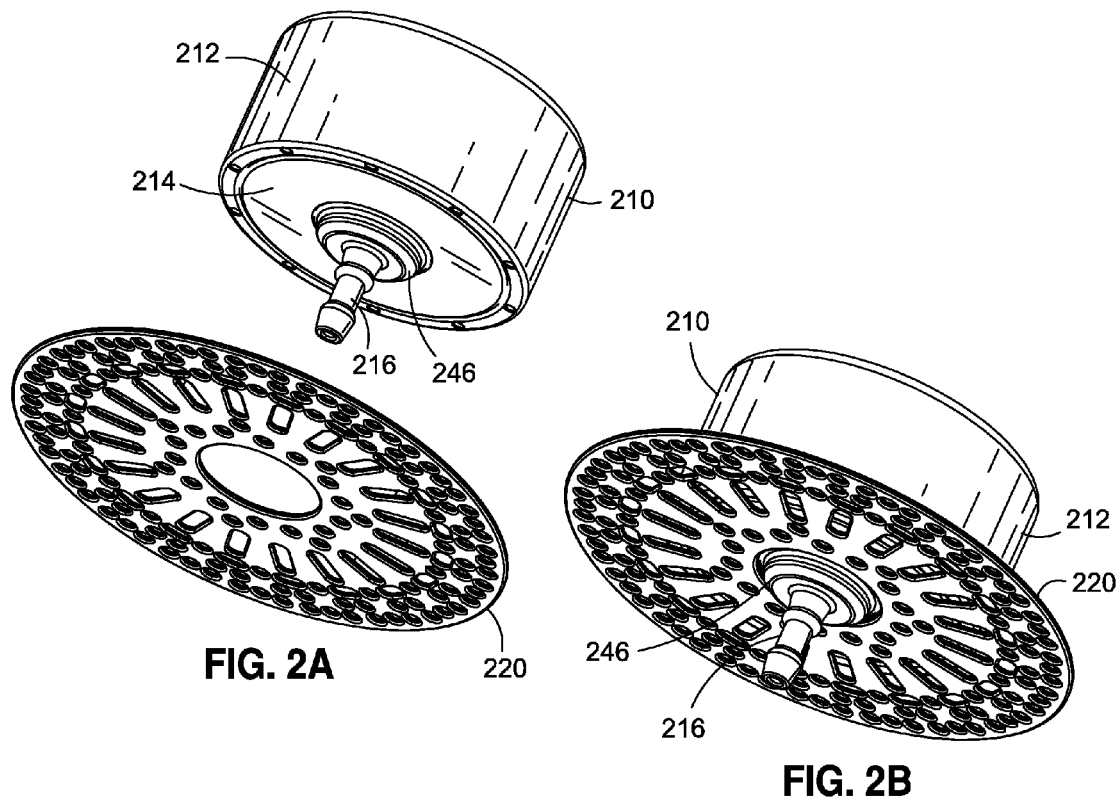
FIG. 2A
FIG. 2B
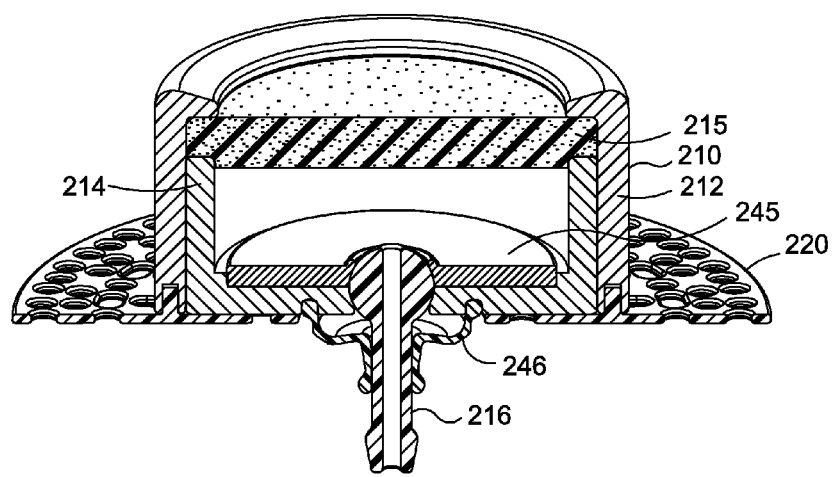
FIG. 2C

IMPLANTABLE BOTTOM EXIT PORT

RELATED APPLICATIONS

This application is a continuation-in-part of, and claims priority to and the benefit of U.S. patent application Ser. No. 12/904,422, entitled "IMPLANTABLE COUPLING DEVICE" filed on Oct. 14, 2010, which is a continuation-in-part of U.S. patent application Ser. No. 12/772,039, entitled "SYSTEM INCLUDING ACCESS PORT AND APPLICATOR TOOL" filed on Apr. 30, 2010, which claims priority to and the benefit of U.S. Provisional patent application No. 61/237,641, filed on Aug. 27, 2009, and U.S. Provisional patent application No. 61/236,869, filed on Aug. 26, 2009, all of these applications are hereby expressly incorporated by reference herein.

FIELD

The present invention generally relates to medical systems and apparatus and uses thereof for treating obesity or obesity-related diseases, and more specifically, relates to access ports and methods for applying the same to bodily tissue.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, the food held in the upper portion of the stomach may provide a feeling of satiety or fullness that discourages overeating. Unlike gastric bypass procedures, gastric band apparatus are reversible and require no permanent modification to the gastrointestinal tract.

Medical implants, including gastric band systems, for performing therapeutic functions for a patient are well known. Such devices include pace makers, vascular access ports, injection ports (such as used with gastric banding systems) and gastric pacing devices. Such implants need to be attached, typically subcutaneously, in an appropriate place in order to function properly.

Many implantable medical devices are secured with sutures. For example, when inserting a gastric band and an associated access port, the associated access port may be sutured into place with sutures against the rectus muscle sheath. Such placement of the sutures is often challenging because the associated access port is placed below several inches of bodily tissue (e.g., fat), and suturing the associated access port often takes as long as placing the gastric band itself.

Additionally, the sutures can cause post surgical pain for the patient due to the inherent pulling and slight tearing of the tissue pieces by and adjacent to the suture.

Also, it is common for medical professionals desiring to add or remove fluid via a needle through the access port to palpitate the skin to locate the implanted port. The medical professional has a general idea of the top surface of the port, but occasionally will accidentally miss the septum and puncture the tube and/or tissue surrounding or adjacent to the port.

Further, some body-related systems utilize retention geometry for the access port attachment such as Bestetti, et al., U.S. Pat. No. 6,270,475. However, Bestetti discloses a percutaneous access port not a subcutaneous access port. Similarly, Svensson, et al., U.S. Pat. No. 5,098,397, discloses a percutaneous access port not a subcutaneous access port.

Accordingly, there remains a need for a procedure to implant medical devices in a quick, easy and efficient manner, utilizing as small of an incision as possible which reduces the likelihood of future discomfort for the patient and protects the elements from errant needle strikes.

SUMMARY

The present invention, in one embodiment, includes an implantable fluid access port of an adjustable gastric banding system coupled to the tissue of a patient. The port is configured to facilitate fluid transfer to and from the gastric banding system. The device includes a top housing section including a top opening, a septum surface, a bottom exit tube coupling, and a bottom housing section with a substantially circular side wall. A partial interior vessel may be formed between the fluid seal created between the bottom surface of the septum and the interior surfaces of the bottom housing portion.

In some embodiments, the implantable port may be configured to shield a coupled tube from inadvertent needle puncture using at least one of the orientation of the bottom exit tube coupling, needle entry orientation, or the structures of the body of the implantable port. The bottom exit tube coupling may be configured to provide a partial anchoring of the implantable port in a pre-selected position.

The device may include a porous coupling member having a top surface and a bottom surface. The porous coupling member may be integral to the implantable fluid access port or coupled to the implantable fluid access port via a coupling agent proximate to the top surface of the porous coupling member for mating with the base of the implantable access port. The porous coupling member may extend in a plane substantially parallel to the base of the bottom housing section and may be configured for anchoring the port to the tissue of the patient. The porous coupling member may be made from injection moldable plastic or rubber. The porous coupling member may be formed as a partial ring shape or a substantially circular shape. The porous coupling member may extend in a plane substantially parallel to the base of the port, including a first portion (proximate to the implantable access port) and a second portion. The first portion may not include a porous surface and the second portion may include a porous surface. The surface that does not include a porous surface may be configured to shield a portion of the patient from contact with a needle.

The implantable fluid access port may further include a guard plate configured to shield the bottom exit tube coupling and/or a tube from contact with a needle. The guard plate may include channels or openings configured to allow fluid to pass from the partial interior vessel to the bottom exit tube coupling. The guard plate may be internal to the partial interior vessel. The bottom housing section may include surface features for positioning a guard plate and/or channeling fluid from the partial interior vessel to the bottom exit tube coupling.

In one embodiment, the bottom exit tube coupling may further include a ball joint socket structure and/or coupling technique. In this embodiment, the bottom exit tube coupling may include a boot.

In some embodiments, the bottom exit tube coupling may be made from a silicon rubber material. The top housing section and the bottom housing section may couple together to place the septum surface under compression. The top housing section and the bottom housing section may be securably coupled together via locking tabs.

In some embodiments, the implantable fluid access port may further include a mesh material oriented between the implantable access port and a coupling member. A through hole in the mesh material may be configured to allow the coupler to pass through the through hole to mate with the base of the implantable access port. This way, the mesh may be sandwichably held in position. The mesh material may be a pre-fabricated mesh material made from injection moldable plastic or rubber. The port may be implanted subcutaneously.

In one embodiment, a method of securably coupling an implantable fluid access port of an adjustable gastric banding system configured to facilitate fluid transfer to and from the gastric banding system is disclosed. The method may include subcutaneously coupling an implantable fluid access port having a bottom exit tube coupling to the tissue of a patient, and coupling the tube of an adjustable gastric banding system to the bottom exit tube coupling.

The method may include protecting the bottom exit tube coupling via a guard plate internal to the port. In some embodiments, the bottom exit tube coupling is made from a silicon rubber material. The port may include a septum configured to receive a needle for fluid transfer. The subcutaneous coupling may be performed via a mesh material oriented between the implantable access port and a coupling member, sutures, and/or using a porous coupler.

These and other aspects and embodiments of the present invention may be more clearly understood or appreciated by referring to the accompanying drawings and the detailed description.

BRIEF DESCRIPTION OF THE DRAWINGS

FIG. 1A illustrates a gastric band port according to an embodiment of the present invention.

FIG. 1B illustrates the gastric band port of FIG. 1A and a coupling device according to an embodiment of the present invention.

FIG. 1C illustrates the gastric band port of FIGS. 1A and 1B and the coupling device of FIG. 1B secured to the tissue of a patient according to an embodiment of the present invention.

FIG. 2A illustrates an implantable access port comprising a ball and socket bottom exit tube coupling and a coupling device according to an embodiment of the present invention.

FIG. 2B illustrates the access port and the coupling device of FIG. 2A mated together according to an embodiment of the present invention.

FIG. 2C illustrates a side cut-away view of the port and the coupling device of FIG. 2B according to an embodiment of the present invention.

DETAILED DESCRIPTION

Figure 1D:
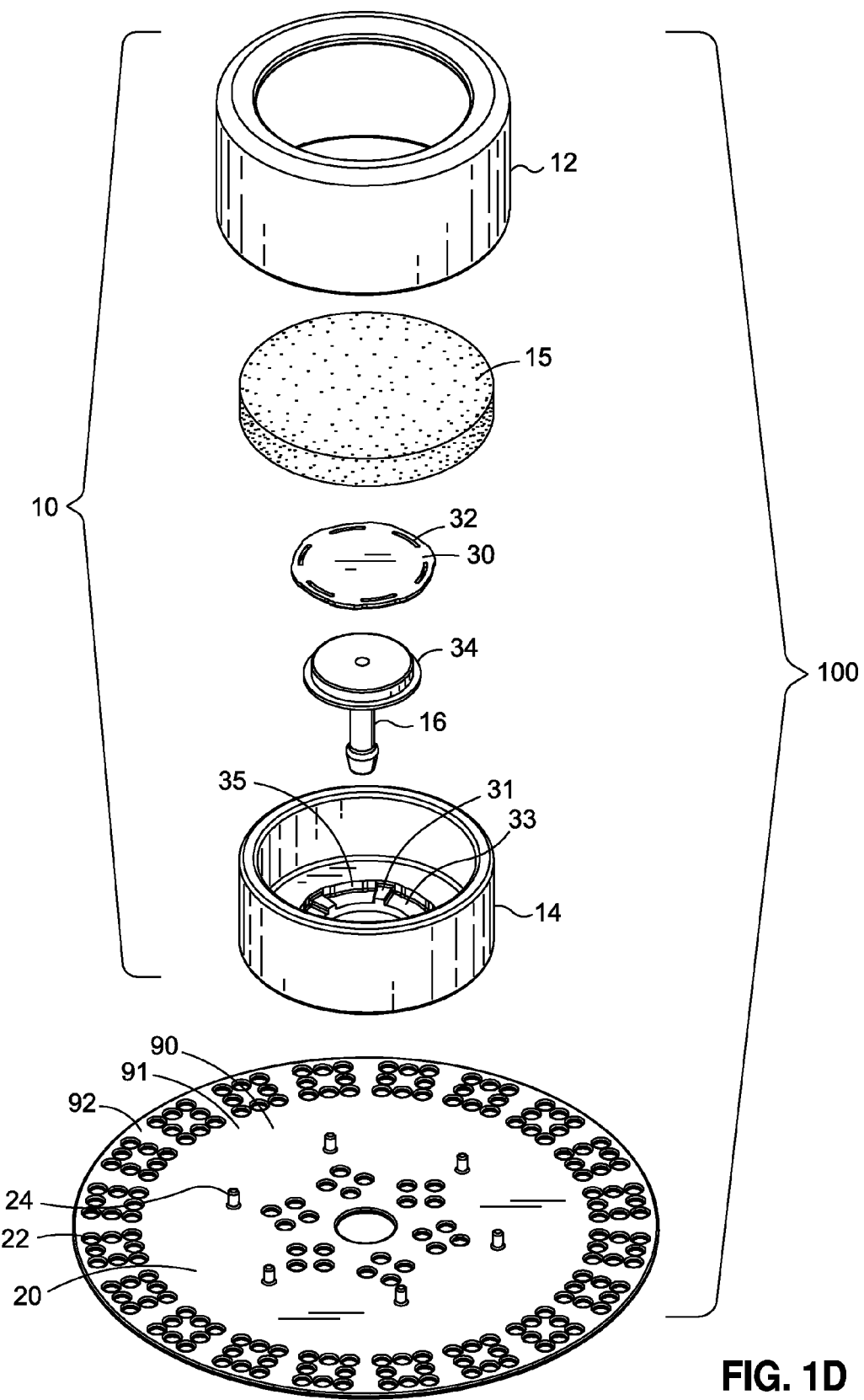
FIG. 1D illustrates an exploded view of the components of the port of FIG. 1A according to an embodiment of the present invention.

The present invention relates to implantable medical devices and fasteners therefore and more specifically to access ports and methods for applying the same to bodily tissue. Specifically, the present invention is directed to a subcutaneous implantable gastric banding system including a subcutaneously attached access port coupled to bodily tissue. In some embodiments, a tube and component guard plate, a flexible exit tube coupling and/or a flexibly oriented exit tube coupling, bottom exit tube orientation and/or a tissue guard may reduce pain caused by errant needle sticks/strikes or reduce the need for follow-up surgery to repair damaged components.

In various embodiments, the present invention utilizes tube guards, component guards, tissue shields, pre-fabricated mesh and porous coupling devices and/or combinations thereof to protect the patient from unnecessary pain or discomfort. In some embodiments, a mesh material and/or coupling device (described in greater detail below) may be used to anchor an access port to a patient's tissue. For example, the mesh material may encourage tissue ingrowth or tissue engagement through holes and spaces of the mesh material. This use of mesh materials to anchor the access port using the patient's own tissue engagement may obviate the need for sutures during implantation. For example, where access port implantation may occur using sutures, during recovery and beyond, movement of the patient may cause discomfort due to a pulling and slight tearing of the tissue around the implantation site. Use of a porous coupling device or prefabricated mesh material according to embodiments of the present invention may eliminate or substantially reduce this discomfort.

In accordance with various embodiments, FIGS. 1A-1D illustrate simplified views of an access port 10 for use in conjunction with an implantable medical device, such as an implantable gastric banding system. The access port 10 may comprise a septum 15 for passing fluid into the access port 10, or removing fluid by means of the access port 10, via a needle. The access port 10 may provide a convenient means for inflating and/or deflating a conventional gastric band, thereby enabling adjustment of a size of a stoma or a level of restriction on a patient's stomach. A tube 6, coupled to or integral to the access port 10, passes the fluid from the access port 10 to and from the gastric band. The access port 10 is generally fixed within the interior of a patient's body, preferably secured to a patient's abdominal muscle.

In various embodiments, the access port 10 comprises at least one anchoring surface 8. The anchoring surface 8 may comprise any suitable anchoring surface, such as a latch, clip, hole, ridge, recess, surface deformity, notch, flange and/or the like. The housing of the access port 10 may comprise any suitable geometry, such as conical, cylindrical, square, block, and/or the like. The side wall of the housing of the access port 10 may comprise a surface transition to assist the operation of the anchoring surface 8.

With continued reference to FIG. 1B, and in accordance with various embodiments, a coupler 20 for assisting with the anchoring of the port 10 is depicted. The coupler 20 may comprise any suitable geometry. In one embodiment, the perimeter of the coupler 20 is larger than and extends away from the port 10 in a plane parallel to the bottom surface of the base of the housing of the port 10. The portion of the coupler 20 extending beyond the base of the housing may extend outwardly from and substantially circumscribe the base, or may extend only partially around the base of the port 10. The coupler 20 comprises a top surface and a bottom surface. The side surface of the coupler 20 may be any suitable shape such as curved or straight with any suitable thickness. The top surface of the coupler 20 comprises coupling agents 24 configured to attach the coupler 20 to the base of the port 10. These coupling agents 24 may be any suitable material and shape. For example, these coupling agents 24 may be glue, epoxy, welds, such as ultrasonic welding, posts, surface features, knobs, bolts, screws, barbs, clamps, clips and/or the like, and combinations thereof.

In one embodiment, as illustrated in FIG. 1B, the coupling agent 24 comprises one or more posts configured to create an interference fit with an opening of the anchoring surface 8 of the port 10. This interference fit may be a press fit, a friction fit, or a push fit. In one embodiment, the coupling agent 24 may be configured to latch onto the previously described surface transition of a side wall of the port 10 housing (not depicted). In various embodiments, the coupler 20 may be integrally molded into or as part of the base of the housing of the port 10.

Further, in an embodiment, a portion of the coupler 20 may be porous. For example, a plurality of through holes 22 may pass from the top surface to the bottom surface of the coupler 20. These through holes 22 may be configured to allow for tissue ingrowth or tissue engagement through the through holes 22 to serve as or assist with the anchoring of the port 10 with the patient. The through holes 22 may be formed in any configuration. For example, the spacing of the holes may be regular or irregular. The through holes 22 may be formed in substantially the entire surface of the coupler 20 or the through holes 22 may be located in a particular portion(s) of the coupler 20. For example, the through holes 22 may be located towards the outer perimeter of the coupler 20 leaving a portion of the surface without through holes 22 proximate the base of the port 10.

Further, in accordance with various embodiments, FIG. 1B illustrates a perspective view of the coupler 20 having a tissue shield 90. For example, the coupler 20 may comprise a first portion 91 without the through holes 22 and a second portion 92 having the through holes 22. The first portion 91 without the through holes 22 may act as a tissue guard protecting the surface underneath the first portion 91 from contact with the needle. The likelihood of errant needle sticks/strikes is proportional to the distance from the access port 10. Stated another way, as the distance away from the access port 10 increases, the likelihood of errant needle strikes decreases. Thus, in one embodiment, the second portion 92 comprising through holes 22 is located towards the exterior perimeter of the coupler 20 and the first portion 91 without the through holes 22 is located near the access port 10. In this embodiment, though it may be any suitable length, the tube guard 60 extends from the access port 10 to the outer perimeter of the coupler 20.

In one embodiment, the coupler 20 may comprise one or more flanges (not depicted) configured to support the flexing of the anchoring surface of the patient, such as the patient's abdominal wall adjacent to and coupled to the bottom surface of the coupler 20. For example, the flange 26 may be formed by forming a groove in the coupler 20. The coupler 20 may be made from any suitable material. For example, the coupler 20 may be made from an injection molded plastic material, injection molded rubber material, compression molded material, transfer molded material, over-molded plastic over mesh, and/or the like. In one embodiment, the coupler 20 may be integral to a surface, such as the bottom surface of the port 10.

Turning now to FIG. 1C, in accordance with an embodiment, the top surface of the coupler 20 is depicted as being mated with the bottom surface of the port 10. At least a portion of the coupler 20 extends beyond the bottom surface of the port 10. The coupling agents 24 are sized to create an inference fit with the anchoring surface 8 of the port 10 to facilitate connecting the coupler 20 to the port 10. The bottom surface of the coupler 20 is depicted as being mated with the top surface of a portion of the patient such as the tissue of the patient. A portion of the coupler 20 may be used as an attachment point to suture, staple, tack or otherwise fasten the access port 10 to the patient's body.

With further reference to FIG. 1C, according to an embodiment, a portion of the through holes 22 allows tissue growth up through the through holes 22 and above the top surface of the coupler 20. A portion of the through holes 22 allows tissue growth up through the through holes 22 to the bottom surface of the port 10. In one embodiment, a spacer disposed between, on, near, or integral to the coupling agents 24 creates a gap between the coupler 20 and the bottom surface of the port 10 to allow tissue growth through substantially one or more through holes 22.

In this manner, the body's own tissue may grow into the coupler 20 and act as an anchoring mechanism. This anchoring mechanism may be more comfortable for the patient post surgery than previous access port anchoring methods and techniques.

In another embodiment, a mesh material may be molded onto a biocompatible material such as injection molded plastic or a rubber coupler having the coupling agents 24. In one embodiment, the pre-fabricated mesh material may be sandwichably oriented between the access port 10 and a clip or coupler. Principles of the present disclosure may suitably be combined with design and principles for implantable ports and mesh material as disclosed in a co-pending U.S. patent application Ser. No. 12/904,422, entitled "IMPLANTABLE COUPLING DEVICE" filed on Oct. 14, 2010, the contents of which is hereby incorporated by reference in its entirety.

Turning now to FIG. 1D an exploded view of an embodiment of the present device 100 is presented. In this embodiment, the port 10 comprises a top housing section 12, a septum 15, a guard plate 30, a bottom exit tube coupling 16, a bottom housing section 14, and a coupler 20.

The top housing section 12 comprises a substantially circular side wall and a substantially ring shaped top opening. The top opening may be sized to permit suitable access to the septum surface 15. The thickness and height of the substantially circular side wall may be any suitable thickness. The interior of the top housing section 20, as shown in FIG. 1D, comprises a substantially circular smooth interior surface.

This substantially circular interior surface may be shaped to mate with a surface of the bottom housing section 14, such as the exterior surface of the bottom housing section 14.

The septum 15 may be any suitable shape or dimension. In one embodiment, the thickness and diameter of the substantially circular septum 15 is sized to be secured in place by an interference fit between the top housing section 12 and the bottom housing section 14. The septum 15 may be made from any suitable material configured to be self-sealing after the puncture of a needle.

The bottom exit tube coupling 16 may be configured to be coupled to the tube 6. In this manner, the bottom exit tube coupling 16 may facilitate the transfer of fluid from the port to the tube 6. The bottom exit tube coupling 16 is oriented to couple with the tube 6 in a direction substantially normal to the bottom surface of the port 10, such as the bottom surface of the bottom housing section 14, away from the port 10. Stated another way, the connection of the port 10 to the tube 6 is downward (e.g. out the bottom of the port).

The first end of the bottom exit tube coupling 16 is shaped and sized for any suitable coupling, such as for an interference fit, with a portion of the bottom housing section 14 (as shown in FIGS. 1C and 1D). The bottom exit tube coupling 16 may be made from a relatively flexible material, such as a silicon rubber material for making a fluid tight connection with the bottom exit tube coupling 16. The second end of the bottom exit tube coupling 16 is shaped and sized for an interference fit with the end of the tube 6 (as shown in FIG. 1C). The second end may fashioned with a surface feature for securably attaching to the tube 6 or the tube 6 may be fashioned with a surface feature for securably attaching to the bottom exit tube coupling 16 or a combination thereof.

Moreover, the bottom exit tube coupling 16 may be made from a relatively flexible (non-rigid) material, such as a silicon rubber material, to provide generous strain relief to movement at the base of the port 10 and/or to aid in reducing the discomfort to the patient as compared with previous rigid tube coupling structures.

The length of the channel on the bottom exit tube coupling 16 between the bottom of the bottom housing section 14 and the connection with the tube 6 may be any suitable length. For instance, the length between the bottom of the bottom housing section 14 and the connection with the tube 6 may be about a centimeter or the length may be tens of centimeters.

As discussed above, the bottom housing section 14 is shaped to securably couple to the top housing section 12 via any suitable coupling method, such as via an interference fit or press fit, or by being clamped, adhered using adhesive, or otherwise coupled to the top housing section 12. The interior of the bottom housing section comprises a substantially ring shaped opening. The bottom surface of the septum 15 and the interior surface of the bottom housing section 14 form a partial interior vessel of the port. The bottom housing section 14 further comprises surface features for housing the guard plate 30. These surface features may include an opening for the guard plate 30 to be press fit into, where the opening is slightly smaller than the diameter of the guard plate 30 creating a tight press fit between the bottom housing section 14 and the guard plate 30. The bottom housing section 14 surface features may be raised support elements 31 to lift the guard plate 30 above a channel(s) 35 in the bottom exit tube coupling 34 and/or the bottom interior surface of the bottom housing section 14 may be fashioned into channels to allow the passage of fluid. For instance, these channels allow the passage of a fluid from the partial interior vessel of the port 10 through strategically placed openings 32 in the guard plate 30 to the bottom exit tube coupling 16 and to the tube 6.

The guard plate 30 may be secured to the bottom housing section 14 by any suitable means, such as through an interference fit. In another embodiment, the guard plate 30 may have more or fewer openings (as compared to FIG. 1D) at regular or irregular intervals in any suitable location on the guard plate 30. The guard plate 30 may be made from any suitable material for protecting device elements from needle strikes. For instance, the guard plate 30 may be made from titanium or stainless steel.

In one embodiment, the openings 32 in the guard plate 30 may be narrow, long openings sized smaller than the diameter of the needle point to reduce the likelihood of the needle becoming stuck in the opening 32. These openings 32 may be placed towards the edge of the guard plate 30 passing from the top surface of the guard plate 30 to the bottom surface of the guard plate 30. The guard plate 30 may be any suitable shape such as a flat disc shape. In other embodiments, the guard plate 30 may be shaped with a tapering bottom or other surface features or markings such as grooves or slots to position the guard plate 30 in a specified orientation.

Figure 1E:
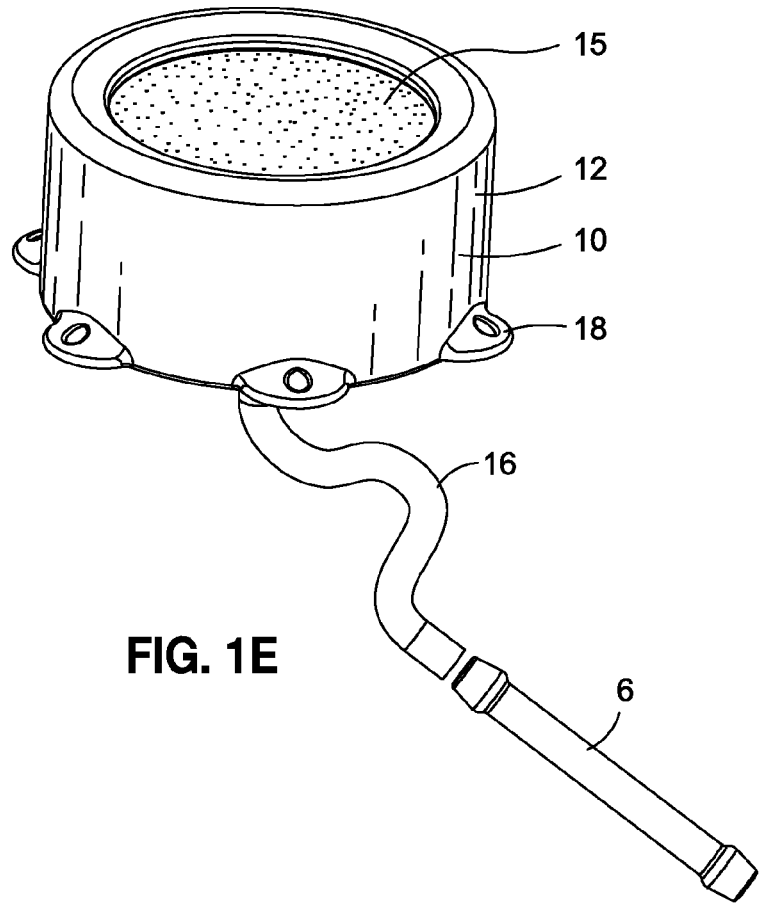
FIG. 1E illustrates a perspective view of a port and a bottom exit extended tube coupling mated with a tube extension according to an embodiment of the present invention.
Figure 1F:
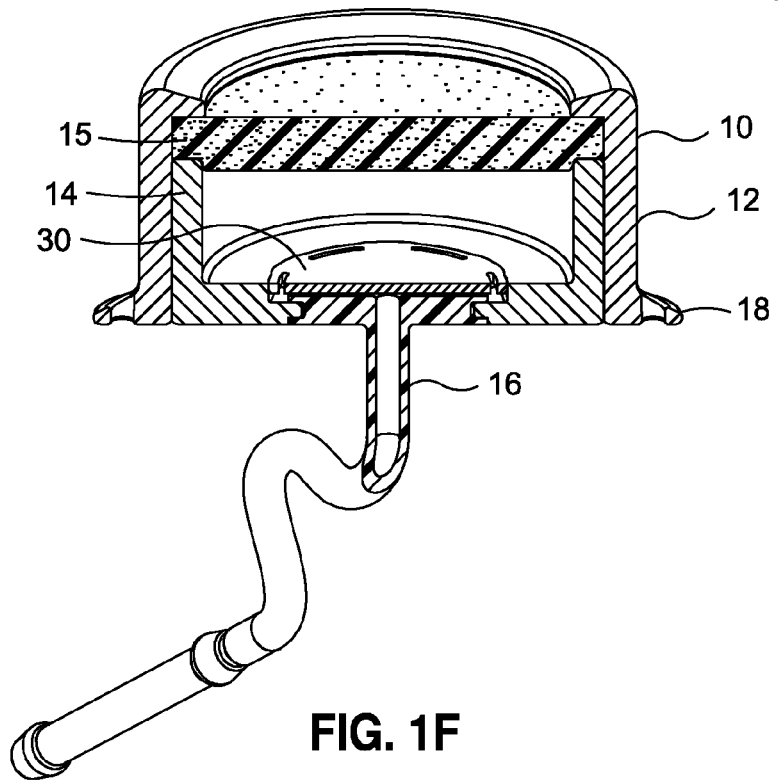
FIG. 1F illustrates a side cut-away view of the port and the bottom exit extended tube coupling of FIG. 1E according to an embodiment of the present invention.

Optionally, and with reference to FIGS. 1E and 1F, the coupler 20 may be replaced with a suture, mesh or other coupling means. For instance, the exterior of the top housing section 12 may be fashioned with surface features 18, such as suture holes, to suture the port 10 to a patient.

An implantable port device 210 according to various embodiments is depicted in FIGS. 2A-2C. In such embodiments, the implantable port device 210 comprises a top housing section 212, a septum 215, an optional guard plate (not shown), a bottom exit tube coupling 216, a bottom housing section 214, a boot 246, a top plate 245 and a coupler 220.

The interface between the first end of the bottom exit coupling 216 and the bottom housing section 214 is a fluid tight ball joint system. This ball joint system may include a rounded top section configured to sit in a mating rounded bottom opening of the bottom housing section 214 having a slight taper. In this manner the bottom exit coupling 216 may move and/or rotate without losing the fluid seal in the internal vessel.

In this embodiment, the orientation of the tube 6 and/or the position of the surrounding tissue can dictate the orientation of the bottom exit tube coupling 216. This may reduce discomfort by the patient and reduce stress and strain on the tube 6 as the patient moves. In this embodiment, the bottom exit coupling 216 may be made from any suitable material such as a rubber or a semi-rigid or rigid medical grade plastic or polymer.

A top plate 245 (as shown in FIG. 2C) may be used for securing the ball joint into position. Stated another way, the bottom exit coupling 216 ball joint may be fed through the opening in the bottom housing section 214 and then a top plate 245 may sandwichably create a sealing joint which allows for pivoting movements due to a low coefficient of friction of the mating materials. The top plate 245 may be secured to the bottom housing section 214 by any suitable means, such as by a press fit, or by being clamped, or adhered using adhesive. In some embodiments, the single opening in the ball joint bottom exit coupling 216 leading from the partial internal vessel may be replaced with one or more smaller holes which couple to the interior channel. This configuration may reduce the chance of the needle becoming stuck in the opening of the ball joint bottom exit coupling 216. In some embodiments, the ball joint of the bottom exit coupling 216 may pivot up to a 30 degree angle from a central axis in 360 degrees around the axis.

Optionally, a boot 246 may be coupled around a portion of the bottom exit coupling 216 and to the bottom exterior surface of the bottom housing section 214 to form a secondary fluid seal. The boot 246 may be coupled to the bottom exit coupling 216 by any suitable means such as a press fit. Also, the boot 246 may be coupled to the bottom housing section 214 by any suitable means, such as with a press fit and/or by being adhered. The boot 246 may be made from any suitable material, such as a flexible rubber material.

In one embodiment, a guard plate 230 may be coupled to the partial interior vessel of the port 210 to protect the internal port 210 elements from needle strikes. Optionally, the coupler 220 may be replaced with a suture, mesh or other coupling means.

Another configuration of an implantable port device 310, according to various embodiments, is depicted in FIGS. 3A-3D. In such embodiments, the implantable port device 310 comprises a top cap 352, a septum 315, an internal ring 354, one or more lock tabs 356, a guard plate 330, a molded flange 358, and a bottom cap 360. The implantable port device 310 may be a low cost option which does not require some of the press fit couplings of previously described embodiments.

The septum 315 may be inserted up, into and/or partially through the top cap 352. The internal ring 354 may be placed between the guard plate 330 and the septum 315. The molded flange 358 may be inserted down into and at least partially through the bottom cap 360. The septum 315, the internal ring 354 and the guard plate 330 may be inserted into the bottom cap 360. The septum 315 and the top cap 352 may be mated with the bottom cap 360 and other elements of port 310. One or more locking tabs 356 may be inserted into apertures to securably couple the top cap 352 to the bottom cap 360. An internal fluid seal is created by assembling the implantable port device 310 as described above.

In one embodiment, the septum 315 may be made from silicon rubber. The formed rim of the septum 315 is under compression creating a fluid tight seal after assembly is complete. The internal ring 354 holds down the guard plate 330 and aids in creating the seal against the septum 315.

Figure 3A:
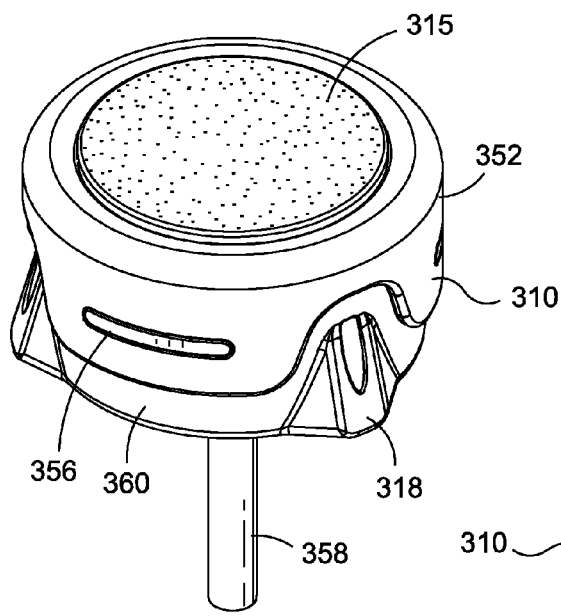
FIG. 3A illustrates a perspective view of an alternative port according to an embodiment of the present invention.
Figure 3B:
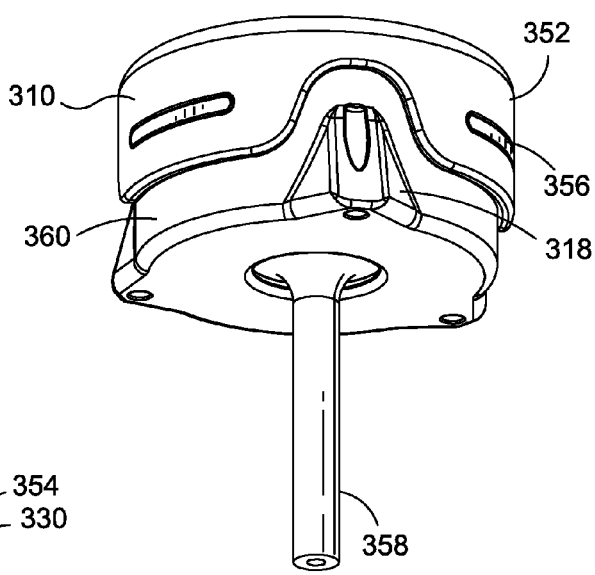
FIG. 3B illustrates a perspective bottom view of the port of FIG. 3A according to an embodiment of the present invention.
Figure 3C:
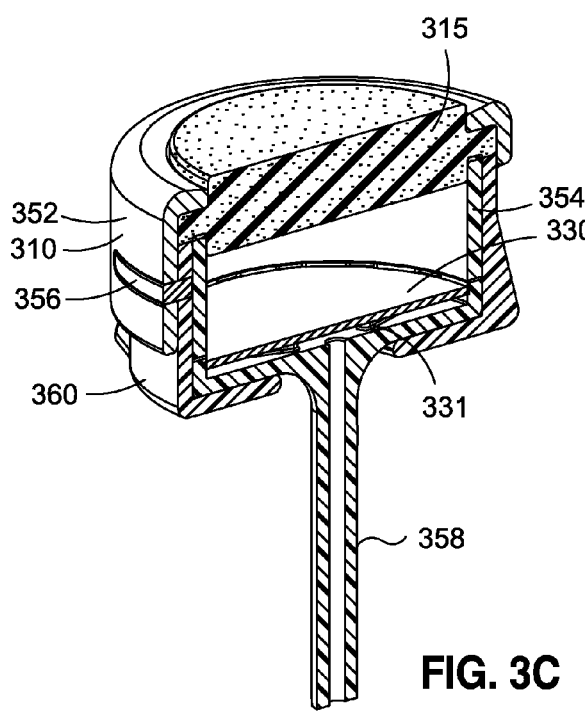
FIG. 3C illustrates a side cutaway view of the port of FIG. 3A according to an embodiment of the present invention.
Figure 3D:
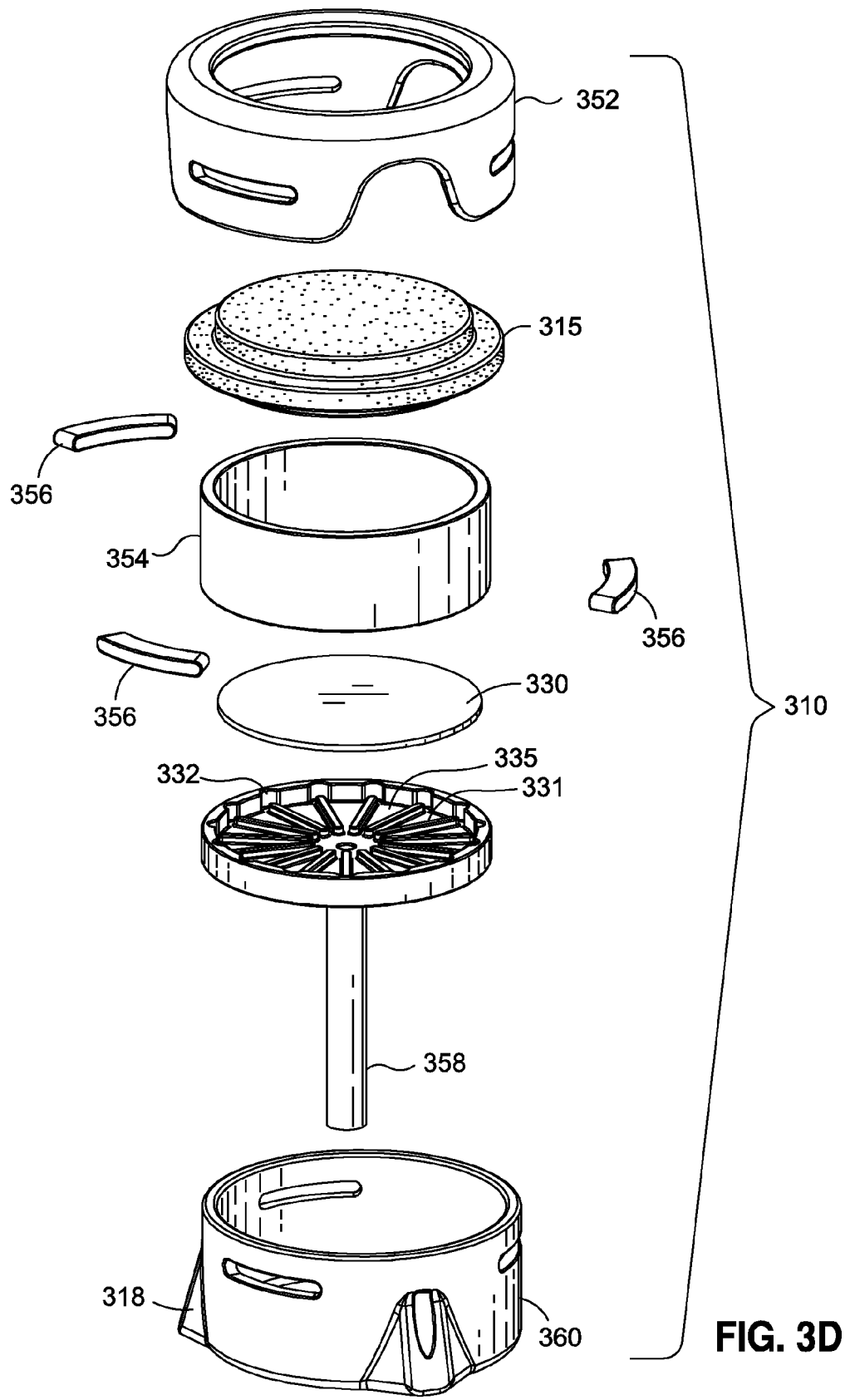
FIG. 3D illustrates an exploded view of the components of the port of FIG. 3A according to an embodiment of the present invention.

In one embodiment, as shown in FIG. 3C, a slight radial interference between the guard plate 330 and the molded flange 358, plus compression by the internal ring 354, positions the guard plate 330 in place. In some embodiments, the top cap 352, the septum 315, the internal ring 354, and the bottom cap 360 comprise semi-rigid to rigid materials while the one or more locking tabs 356, the septum 315, and the molded flange 358 comprise soft flexible materials. The interference between the rigid components and the soft rubber components create a fluid seal and maintain a load on the locking tabs 356 to hold the locking tabs 356 in place over time.

The clearance between the edge of the metal plate and several locations (such as indentations 332) on the molded flange 358 allow the fluid internal to the port 310 to transfer from the internal vessel of the port 310 to the molded flange 358 through the channels 335 molded into the geometry of the molded flange 358. Additionally, structural support to lift the guard plate 330 above the channels 335 is provided by molded portions 331 in the molded flange 358. In an embodiment, the coupler 318 may be replaced with a porous coupling member, mesh or other coupling means. The molded flange 358 may be made of any suitable material for flexing, such as molded silicon rubber. Additionally, strain relief on the molded flange 358 may be increased if desired by altering the geometry of the molded flange 358.

The conduit towards the bottom of and integral to the molded flange 358 may be made from any suitable material. For instance, the molded flange 358 may be made from one or more materials such as silicon rubber. A silicon rubber conduit allows for generous strain relief at the potential flex points with no metal or rigid stem connector. The rigid stem connector may increase the joint stress at the tube 6 coupling point.

Figure 4:
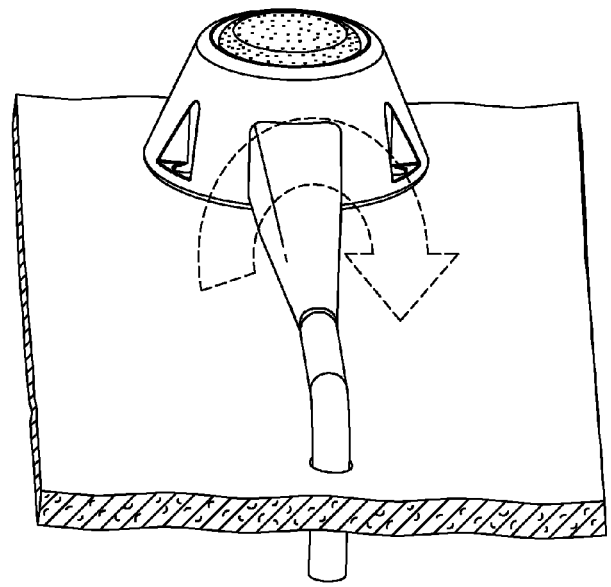
FIG. 4 illustrates an implantable access port comprising a side exit tube coupler according to an embodiment of the present invention.

Previous ports have utilized side exiting and/or rigid tube coupling structures (as depicted in FIG. 4). These structures may be susceptible to strain and/or needle puncture. Moreover, these side exiting tube 6 coupling structures often utilize an eventual turn of the tube 6 from the relatively horizontal direction to a relatively vertical position depending on the implantation point of the port. This places the tube 6 under stress and under strain at the point of change in direction. Additionally, if these side exiting ports are not suitably secured to the tissue of the patient, they may become misaligned. The flexible down stream tube 6 inserted in the patient may not provide support for the unsecured side exiting ports. For instance, an improperly secured side exit port may flip partially over or become inverted (as depicted by the arrow in FIG. 4). A partially flipped or inverted port may be unsuitable for fluid transfer via needle and/or require a surgical procedure to re-orient the device. For instance, the septum surface may be inaccessible by a needle.

Figure 5A:
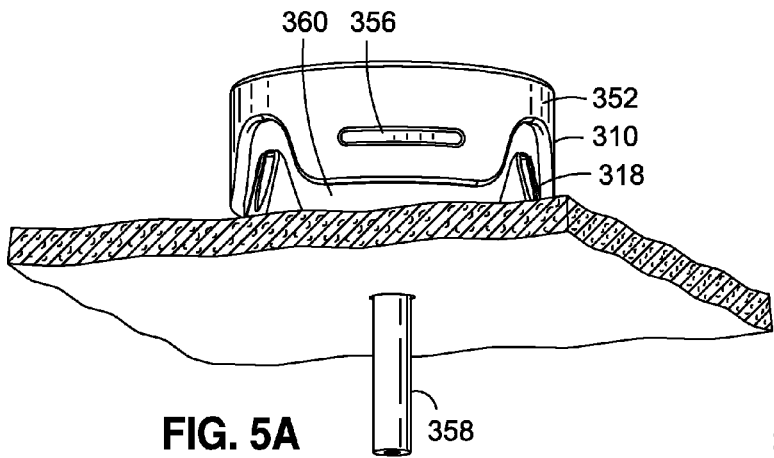
FIG. 5A illustrates a perspective view of an implantable access port comprising a bottom exit tube coupler positioned directly in the tissue of a patient according to an embodiment of the present invention.
Figure 5B:
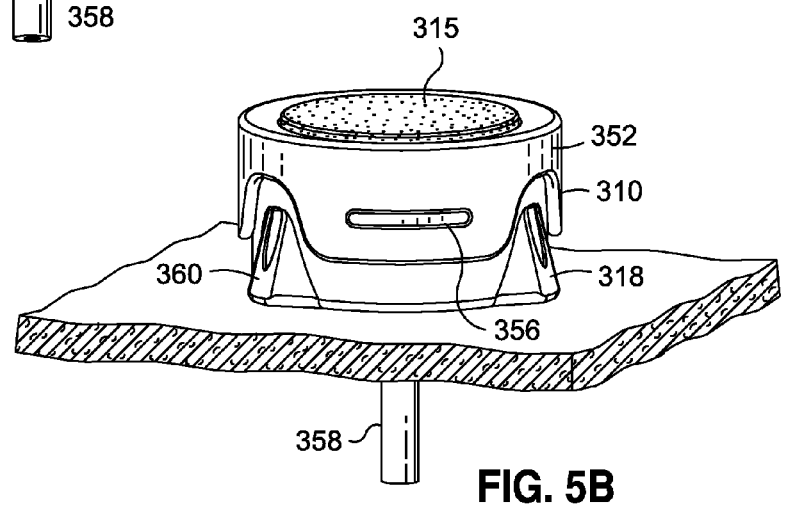
FIG. 5B illustrates a top perspective view of the access port of FIG. 5A according to an embodiment of the present invention.

The bottom exit tube coupling 358 orientation in the downward direction (relative to the base of the port 310) reduces the stress and strain placed on the tube 6 by reducing the need to bend the tube 6 from the relatively horizontal direction to the relatively horizontal direction as compared with a side exiting tube coupling. Also, the orientation of the bottom exit tube coupling 358 naturally protects the tube 6 from needle puncture. In this manner, the body of the implantable port 310 and the direction of needle insertion substantially in line with the bottom exit tube coupling 358 may protect the needle from puncture. Additionally, the physical structure of the bottom exit tube coupling 358, which exits via the base of the port 310 substantially inline with the needle insertion direction, stabilizes the position of the port 310. This physical structure (i.e., a bottom exit port coupling 358 as shown in FIGS. 5A and 5B) reduces the likelihood that the port 310 will become misaligned and/or partially flip or invert. In some embodiments, a bottom exiting port coupling will physically not be able to flip after insertion in the tissue of the patient. In this manner, the bottom exit port coupling 358 functions as an anchor and/or partial anchor of the device in a pre-selected orientation and/or position. This may also orient the implantable port 310 in a position where the septum is easily targeted by an approaching needle. In some embodiments, the exterior surface of the bottom exit coupler 358 may be altered to comprise surface features for securing and or orienting the port 310. For instance, in an embodiment, the exterior surface of the bottom exit coupler 358 may be barbed.

In one embodiment, the elements of the implantable port and/or coupler may be coated with a bioresorbable material, for example, to encourage biological compatibility between the device elements and the body tissue. The coating may cover the entirety of the device elements or only a portion of the device elements. A thickness of the coating may be even, or may vary along the surface of the device elements. The coating may be deposited through a process including a spraying process, dipping process, molding process, wiping process, or other equivalent means of attaching the bioresorbable material to the device elements. The coating thickness may vary between approximately 0.001 inches and 0.25 inches. The bioresorbable material serves to form a biological seal between the access port 10 and the body tissue, and to encourage compatibility between the access port 10 and the body tissue.

The implantable ports described herein may comprise any suitable shape. For instance, the ports may be generally conical, cylindrical, cubical, rectangular prism, or irregularly shaped. In this manner, the ports may comprise substantially circular side walls or non-circular side walls. Also, the ports may comprise top and bottom surfaces with any suitable geometric or non-geometric shape.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable access port for use with a gastric band for the treatment of obesity, the implantable access port comprising:
   a septum surface;
   a top housing section comprising a top opening for the septum surface;
   a bottom exit tube coupling that provides a partial anchoring of the implantable access port in a pre-selected position;
   a bottom housing section, wherein a partial interior vessel is formed by a fluid seal created between a bottom surface of the septum surface and an interior surface of the bottom housing section; and
   a porous coupling member having a top surface and a bottom surface, said porous coupling member having a first portion extending substantially parallel to a base of the bottom housing section, wherein the first portion does not comprise a porous surface and a second portion extending substantially parallel to the base of the bottom housing section, wherein the second portion comprises a porous surface, and wherein the first portion is configured to shield a portion of a patient from contact with a needle.

2. The implantable access port of claim 1, wherein the implantable port is configured to shield a coupled tube from inadvertent needle puncture using at least one of an orientation of the bottom exit tube coupling, needle entry orientation, or structures of a body of the implantable port.

3. The implantable access port of claim 1, wherein the porous coupling member is at least one of integral to the implantable access port or coupled to the implantable access port via a coupling agent proximate the top surface of the porous coupling member for mating with the base of the implantable access port.

4. The implantable access port of claim 1, wherein the porous coupling member extends substantially parallel to the base of the bottom housing section, and
   wherein the bottom surface of the porous coupling member is configured for anchoring the porous coupling member to a tissue of a patient.

5. The implantable access port of claim 1, wherein the porous coupling member is made from injection moldable plastic or rubber.

6. The implantable access port of claim 1, wherein the porous coupling member is at least one of a partial ring shape or a substantially circular shape.

7. The implantable access port of claim 1, wherein the first portion is proximate to the implantable access port.

8. The implantable access port of claim 1, wherein the bottom housing section further comprises surface features for at least one of positioning a guard plate or channeling fluid from the partial interior vessel to the bottom exit tube coupling.

9. The implantable access port of claim 1, wherein the top housing section and the bottom housing section couple together to place the septum surface under compression.

10. The implantable access port of claim 9, wherein the top housing section and the bottom housing section are securably coupled together via lock tabs.

11. An implantable access port for use with a gastric band for the treatment of obesity, the implantable access port comprising:

a septum surface;
a top housing section comprising a top opening for the septum surface;
a bottom exit tube coupling that provides a partial anchoring of the implantable access port in a pre-selected position;
a bottom housing section, wherein a partial interior vessel is formed by a fluid seal created between a bottom surface of the septum surface and an interior surface of the bottom housing section;
a mesh material oriented between the implantable access port and a coupling member; and
a through hole in the mesh material configured to allow the coupling member to pass through the through hole to mate with a base of the implantable access port.

12. The implantable access port of claim 11, wherein the mesh material is a pre-fabricated mesh material made from injection moldable plastic or rubber.

13. The implantable access port of claim 11, wherein the port is configured to be implanted subcutaneously.

14. A method of securably coupling to a tissue of a patient an implantable access port of an adjustable gastric banding system configured to facilitate fluid transfer to and from the gastric banding system, the method comprising:
subcutaneously coupling an implantable fluid access port having a bottom exit tube coupling to the tissue of the patient, the bottom exit tube coupling made from a silicon rubber material and is configured to provide a partial anchoring of the implantable access port in a pre-selected position, wherein the port comprises a septum configured to receive a needle for fluid transfer; and
coupling a tube of the adjustable gastric banding system to the bottom exit tube coupling.

15. The method of claim 14, further comprising protecting the bottom exit tube coupling via a guard plate internal to the port.

16. The method of claim 14, wherein the subcutaneous coupling is performed via at least one of a mesh material oriented between the implantable access port and a coupling member, sutures, or a porous coupler.

17. An implantable access port for use with a gastric band for the treatment of obesity, the implantable access port comprising:
a septum surface;
a top housing section comprising a top opening for the septum surface;
a bottom exit tube coupling that provides a partial anchoring of the implantable access port in a pre-selected position;
a bottom housing section, wherein a partial interior vessel is formed by a fluid seal created between a bottom surface of the septum surface and an interior surface of the bottom housing section; and
a guard plate configured to shield at least one of the bottom exit tube coupling or a tube from contact with a needle, wherein the guard plate comprises channels configured to allow fluid to pass from the partial interior vessel to the bottom exit tube coupling.

18. The implantable access port of claim 17, wherein the guard plate is internal to the partial interior vessel.

19. An implantable access port for use with a gastric band for the treatment of obesity, the implantable access port comprising:
a septum surface;
a top housing section comprising a top opening for the septum surface;
a bottom exit tube coupling comprising a ball joint socket that provides a partial anchoring of the implantable access port in a pre-selected position; and
a bottom housing section, wherein a partial interior vessel is formed by a fluid seal created between a bottom surface of the septum surface and an interior surface of the bottom housing section.

20. The implantable access port of claim 19, wherein the bottom exit tube coupling further comprises a rubber boot.

21. An implantable access port for use with a gastric band for the treatment of obesity, the implantable access port comprising:
a septum surface;
a top housing section comprising a top opening for the septum surface;
a bottom exit tube coupling made from a silicon rubber material wherein the bottom exit tube coupling is configured to provide a partial anchoring of the implantable access port in a pre-selected position; and
a bottom housing section, wherein a partial interior vessel is formed by a fluid seal created between a bottom surface of the septum surface and an interior surface of the bottom housing section.

22. A method of securably coupling to a tissue of a patient an implantable access port of an adjustable gastric banding system configured to facilitate fluid transfer to and from the gastric banding system, the method comprising:
subcutaneously coupling an implantable fluid access port having a bottom exit tube coupling to the tissue of the patient, wherein the port comprises a septum configured to receive a needle for fluid transfer, wherein the subcutaneous coupling is performed via at least one of a mesh material oriented between the implantable access port and a coupling member, sutures, or a porous coupler; and
coupling a tube of the adjustable gastric banding system to the bottom exit tube coupling.

23. A method of securably coupling to a tissue of a patient an implantable access port of an adjustable gastric banding system configured to facilitate fluid transfer to and from the gastric banding system, the method comprising:
subcutaneously coupling an implantable fluid access port having a bottom exit tube coupling to the tissue of the patient, wherein the port comprises a septum configured to receive a needle for fluid transfer;
protecting the bottom exit tube coupling via a guard plate internal to the port; and
coupling a tube of the adjustable gastric banding system to the bottom exit tube coupling.

* * * * *